United States Patent
Brodkin et al.

(10) Patent No.: US 6,994,549 B2
(45) Date of Patent: Feb. 7, 2006

(54) DENTAL RESTORATIONS FORMED BY SOLID FREE-FORM FABRICATION METHODS

(75) Inventors: Dmitri Brodkin, West Orange, NJ (US); Carlino Panzera, Hillsborough, NJ (US); Paul Panzera, Mt. Holly, NJ (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/972,351

(22) Filed: Oct. 5, 2001

(65) Prior Publication Data

US 2002/0033548 A1 Mar. 21, 2002

Related U.S. Application Data

(62) Division of application No. 09/350,604, filed on Jul. 9, 1999, now Pat. No. 6,322,728.

(60) Provisional application No. 60/092,432, filed on Jul. 10, 1998.

(51) Int. Cl.
*A61C 13/08* (2006.01)

(52) U.S. Cl. ..................... 433/202.1; 264/19
(58) Field of Classification Search ............ 433/202.1, 433/212.1, 215, 222.1, 223; 623/17.11, 23.57
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee | |
| 3,926,906 A | 12/1975 | Lee | |
| 4,115,487 A | 9/1978 | Rockett | |
| 4,433,959 A * | 2/1984 | Faunce | 433/222.1 |
| 4,544,359 A | 10/1985 | Waknine | |
| 4,547,327 A | 10/1985 | Bruins | |
| 4,547,531 A | 10/1985 | Waknine | |
| 4,672,032 A | 6/1987 | Slavkin | |
| 4,717,341 A | 1/1988 | Goldberg | |
| 4,789,649 A * | 12/1988 | Abert et al. | 501/3 |
| 4,894,012 A | 1/1990 | Goldberg | |
| 4,937,928 A * | 7/1990 | van der Zel | 29/896.1 |
| 5,002,583 A * | 3/1991 | Pitaru et al. | 623/11.11 |
| 5,104,319 A * | 4/1992 | Evans et al. | 433/202.1 |
| 5,204,055 A | 4/1993 | Sachs | |
| 5,276,068 A | 1/1994 | Waknine | |
| 5,340,656 A | 8/1994 | Sachs | |
| 5,346,397 A | 9/1994 | Braiman | |
| 5,387,380 A | 2/1995 | Cima | |
| 5,444,104 A | 8/1995 | Waknine | |
| 5,490,962 A | 2/1996 | Cima | |
| 5,518,680 A | 5/1996 | Cima et al. | 264/401 |
| 5,587,913 A | 12/1996 | Abrams | |
| 5,679,144 A * | 10/1997 | Thiel et al. | 106/35 |
| 5,684,103 A | 11/1997 | Jia | |
| 5,700,289 A | 12/1997 | Breitbart | |
| 5,900,207 A | 5/1999 | Danforth | |
| 5,940,882 A | 8/1999 | Auguste | |
| 5,947,893 A * | 9/1999 | Agrawal et al. | 600/36 |
| 5,969,000 A | 10/1999 | Yang | |
| 5,989,031 A * | 11/1999 | Kura et al. | 433/202.1 |
| 6,013,694 A | 1/2000 | Jia | |
| 6,039,569 A | 3/2000 | Prasad | |
| 6,143,948 A * | 11/2000 | Leitao et al. | 424/422 |
| 6,186,790 B1 | 2/2001 | Karmaker | |
| 6,376,573 B1 * | 4/2002 | White et al. | 523/115 |

* cited by examiner

*Primary Examiner*—Melba N. Bumgarner
(74) *Attorney, Agent, or Firm*—Ann M. Knab

(57) ABSTRACT

Solid free form fabrication techniques such as fused deposition modeling and three-dimensional printing are used to create a dental restoration. Three-dimensional printing comprises inkjet printing a binder into selected areas of sequentially deposited layers of powder. Each layer is created by spreading a thin layer of powder over the surface of a powder bed. Instructions for each layer may be derived directly from a CAD representation of the restoration. The area to be printed is obtained by computing the area of intersection between the desired plane and the CAD representation of the object. All the layers required for an aesthetically sound restoration can be deposited concurrently slice after slice and sintered/cured simultaneously. The amount of green body oversize is equivalent to the amount of shrinkage which occurs during sintering or curing. While the layers become hardened or at least partially hardened as each of the layers is laid down, once the desired final shaped configuration is achieved and the layering process is complete, in some applications it may be desirable that the form and its contents be heated or cured at a suitably selected temperature to further promote binding of the powder particles.

6 Claims, No Drawings

DENTAL RESTORATIONS FORMED BY SOLID FREE-FORM FABRICATION METHODS

CROSS-REFERENCE TO RELATED APPLICATIONS

This application is a division of U.S. application Ser. No. 09/350,604 filed Jul. 9, 1999 now U.S. Pat. No. 6,322,728 which claims priority to U.S. Provisional Application Ser. No. 60/092,432 filed on Jul. 10, 1998, both which are hereby incorporated by reference.

FIELD OF THE INVENTION

This invention relates to dental restorations made from ceramics, glass-ceramic as well as ceramic-matrix and polymer-matrix composite materials using solid free-form fabrication methods. The invention further relates to bodies fabricated by solid free-form techniques which can provide the matrix or skeleton of dental restorations that can be further or concurrently filled with biomimetic substances.

BACKGROUND OF THE INVENTION

The fabrication of current all-ceramic dental restorations often requires extensive labor and time and the proficiency of highly skilled technicians. Many state-of-the-art dental restorations reveal a sense of artistry that can typically only be achieved manually or "by hand." While aesthetics are preserved with this process, microstructural inhomogeneities may appear, affecting strength and reliability. The industry has attempted to automate this process by, for example, pressing crowns. Although pressable crowns reduce some of the skill time required, about two hours of concerted effort is necessary to complete a crown. Pressed crowns may also suffer from similar strength and reliability problems typical of "hand made" crowns.

Computer assisted design/computer assisted milling (CAD/CAM) processes and equipment have been recently introduced into the dental industry. In these processes, a three-dimensional image of a stump of a tooth is created along with the teeth surrounding the stump in an effort to create a dental restoration which is to be placed over the stump. This image is displayed on a computer screen. Based on the stump and surrounding teeth, the dental technician may then select a tooth from a plurality of tooth forms stored in the computer to best fit the stump. The selected tooth is projected onto the stump until an optimum positioning and fit of the dental restoration is achieved. The digital data concerning the dental restoration thus formed are supplied to a numerically controlled milling machine operating in three dimensions. The milling machine cuts a blank of metal or porcelain material into the dental restoration design based on the data supplied.

Commercially available systems such as CEREC from Siemens, PROCERA® from Nobel Biocare AG, and CICERO® from Cicero Dental Systems, have attempted to reduce labor and increase structural reliability. However, the necessary machining steps limit the choice of materials that can be used in dental restorations and sometimes compromise the strength and/or aesthetics of the finished restoration.

One of the current limitations of the CAD/CAM approach, which is not easy to overcome, is the fact that currently available systems at best produce copings that require veneering layers to provide a natural appearance. Consequently, final processing of the crown is still in the hands of dental technicians which limits the resulting structural reliability of the restoration. The existing commercial CAD/CAM systems are unable to produce full crowns Some of the systems can machine inlays/onlays from a solid ceramic block and are not able to produce crowns or even copings. Others produce copings which make a core of the crown that can fit on the prepared tooth but require additional work by dental technicians to provide final shapes and esthetics. This entails manual building and firing of porcelain layers on top of a coping received from the CAD/CAM facility. Supposedly, one or more systems will be able to automate forming of successive veneering layers of porcelain on top of a CAD/CAM coping which will involve sintering of consecutive porcelain layers following their forming by machining or pressing. This is an automation of steps that are otherwise performed by dental technicians and very well may not be practically advantageous.

One of the key limitations intrinsic to CAM methods is the fact that machining is not competitive technology for mass production of parts and components of any kind including dental restorations, e.g. dentures and crowns. At any given period of time one cutting tool can be used to machine only one part and can not be concurrently used to machine another part.

It is desirable that the automation of the manufacture of dental restorations be conducive to mass production of restorations. It is beneficial that the automation of the manufacture of dental restorations be efficient and useful for a variety of materials.

SUMMARY OF THE INVENTION

These and other objects and advantages are accomplished by the process herein directed to solid free-form (SFF) fabrication of dental restorations. Among solid free-form techniques, dimensional printing and fused deposition modeling are preferred because both ceramic and resin-based composite dental restorations can be produced in solid (e.g. denture teeth) or multilayered form (e.g. crowns). Three-dimensional printing is most preferred for mass-production of dental restorations.

Three-dimensional printing is used to create a dental restoration by ink-jet printing a binder into selected areas of sequentially deposited layers of powder. Each layer is created by spreading a thin layer of powder over the surface of a powder bed. Instructions for each layer may be derived directly from a CAD representation of the restoration. The area to be printed is obtained by computing the area of intersection between the desired plane and the CAD representation of the object. All the layers required for an aesthetically sound restoration can be deposited concurrently slice after slice and sintered/cured simultaneously. The amount of green body oversize is equivalent to the amount of shrinkage which occurs during sintering or curing. While the layers become hardened or at least partially hardened as each of the layers is laid down, once the desired final shaped configuration is achieved and the layering process is complete, in some applications it may be desirable that the form and its contents be heated or cured at a suitably selected temperature to further promote binding of the powder particles. The individual sliced segments or layers are joined by one or more binders to form the three dimensional structure. The unbound powder supports temporarily unconnected portions of the component as the structure is built but is removed after completion of printing.

DESCRIPTION OF THE INVENTION

A number of techniques have been developed in recent years that are known under the generic name of solid free-form (SFF) fabrication or also known as rapid prototyping and are successfully used for net-shape manufacturing of advanced materials (ceramics, polymers) into small and complex shapes. These techniques are similar to CAD/CAM techniques in that the digital representation of the final shape and its implementation is designed and controlled by a computer. However, the machining step in these techniques is substituted by other computer assisted net-shaping techniques including but not limited to three-dimensional printing, selective area laser deposition or selective laser sintering (SLS), electrophoretic deposition, robocasting, fused deposition modeling (FMD), laminated object manufacturing (LOM), stereolithography and photostereolithography. Most of these techniques were developed for net-shaped fabrication of polymeric or wax parts, however, some of them, such as three-dimensional printing and fused deposition modeling can be used to build complex shapes from ceramic or even metallic materials as well. A large variety of ceramic, polymeric and composite materials can be fabricated into complex shapes using these techniques. U.S. Pat. Nos. 5,340,656, 5,490,882, 5,204,055, 5,518,680, 5,490,962, 5,387,380, 5,700,289, 5,518,680, and 4,672,032 are directed to solid free-form fabrication methods and techniques and are hereby incorporated by reference.

In this invention, solid free-form techniques are used to make dental restorations including but not limited to denture teeth, bridges, crowns, onlays and inlays. Among solid free-form techniques, dimensional printing and fused deposition modeling are preferred because both ceramic and resin-based composite dental restorations can be produced in solid (e.g. denture teeth) or multilayered form (e.g. crowns). Three-dimensional printing is most preferred for mass-production of dental restorations.

Similarly to CAD/CAM methods, the design of the restoration is carried by a CAD device which uses at least two inputs: (1) the digital image taken optically directly from a mouth of the patient (optical impression) or created by digitizing the impression/die by contact or by an optical digitizer; and (2) a library of teeth shapes and forms. CAD devices assure both natural-like shape and proper function of the restoration. Both optical and contact digitizers providing input (1) above are described in the literature and some of them are commercially available. The specific techniques may require additional software to build the shape according to the CAD file.

In one of the embodiments of the present invention, a three-dimensional printing machine is used for mass-production of dental restorations including, but not limited to denture teeth, all-ceramic and composite crowns, onlays, and inlays. Suitable printing devices include both those with a continuous jet stream print head and a drop-on-demand stream print head. A high speed printer of the continuous type may be used which has a line printing bar containing approximately 1500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

Three-dimensional printing is used to create a dental restoration by ink-jet printing a binder into selected areas of sequentially deposited layers of powder. Each layer is created by spreading a thin layer of powder over the surface of a powder bed. The powder bed is supported by a piston which descends upon powder spreading and printing of each layer, or conversely, the ink jets and spreader are raised after printing of each layer and the bed remains stationary. Instructions for each layer may be derived directly from a CAD representation of the restoration. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

The three-dimensional printing apparatus includes a powder dispersion head which is driven reciprocally in a shuttle motion along the length of the powder bed. A linear stepping motor assembly is used to move the powder distribution head and the binder deposition head. The powder material is dispensed in a confined region as the dispensing head is moved in discrete steps along the mold length to form a relatively loose layer having a typical thickness of about 100 to about 200 microns. All the layers required for an aesthetically sound restoration can be deposited concurrently slice after slice and sintered/cured simultaneously. The amount of green body oversize is equivalent to the amount of shrinkage which occurs during sintering or curing. Although powder is used herein to identify the material, the material may include particles of any shape including fibers, rod-shaped particles, spherical particles, or any shape or form of material used in the manufacture of dental restorations. An ink jet print head having a plurality of ink-jet dispensers is also driven by the stepping motor assembly in the same reciprocal manner so as to follow the motion of the powder head and to selectively produce jets of a liquid binder material at selected regions thereby causing the powdered material at such regions to become bonded. The binder jets are dispensed along a line of the printhead which is moved in substantially the same manner as the dispensing head. Typical binder droplet sizes are about 15 to about 50 microns. The powder/binder layer forming process is repeated so as to build up the restoration, layer by layer.

While the layers become hardened or at least partially hardened as each of the layers is laid down, once the desired final shaped configuration is achieved and the layering process is complete, in some applications it may be desirable that the form and its contents be heated or cured at a suitably selected temperature to further promote binding of the powder particles. In either case, whether or not further curing is required, the loose, unbounded powder particles are removed using a suitable technique, such as ultrasonic cleaning, to leave a finished restoration.

For effective use, the powder particles should be uniformly deposited at a relatively high rate, the rate being selected in accordance with the application for which the technique is used. For many useful applications the powder particles can preferably be packed at relatively high densities, while in other applications the density may be considerably lower where restorations having greater porosity are desired. Known techniques used in the fields of colloidal science and powder dispersion chemistry can be used to provide the desired uniform depositions of such powders at the required rates and densities. Thus, powders can be dispensed either as dry powders or in a liquid vehicle, such as in a colloidal dispersant or in an aqueous suspension. In the dry state, the desired compaction of particles can be achieved using mechanical vibrating compaction techniques or by applying acoustic energy, i.e., either sonic or ultrasonic vibrations, to the deposited powder or by applying a piezoelectric scraper to the deposited powder.

The ink-jet printing of the binder material should utilize droplets of materials having shrinkage characteristics such that the dimensional tolerances of the restoration being made are maintained upon hardening thereof. While the binder solution must have a relatively high binder content, the viscosity thereof should be low enough so as to be able to flow through the printing head for deposit into the powder material. The binder material should be selected to penetrate the layer and to perform its binding action relatively rapidly in each layer so that the next layer of powder particles can be subsequently applied thereto. When using certain ink-jet technology the binder material may require at least a minimum electrical conductivity, particularly when using currently available continuous jet printing heads, for example, which require enough conductivity to establish charge on the binder solution droplets as they are emitted from the head. Where conductivity cannot be established in the binder, as with certain organic solvents, for example, the binder can be applied using drop-on-demand print heads.

The binder material may have a high binding strength as each layer is deposited so that, when all the layers have been bonded, the component formed thereby is ready for use without further processing. In other cases, it may be desirable, or necessary, to perform further processing of the restoration. For example, while the process may be such as to impart a reasonable strength to the restoration which is formed, once the restoration is formed it can be further heated or cured to further enhance the binding strength of the particles. In some cases, the binder is removed during such heating or firing process, while in others, it can remain in the material after firing. Which operation occurs depends on the particular binder material which has been selected for use and on the conditions, e.g., temperature, under which the heating or firing process is performed. Other post-processing operations may also be performed following the formation of the restoration. The rate at which a ceramic, metal, plastic, or composite restoration can be made depends on the rates used to deposit the powder and to supply the binder liquid, and on the rate at which each bonded layer hardens as the layers are deposited one on the other.

Alumina, zirconia, mullite, silica, spinel, tricalcium phosphate, apatite, fluoroapatite, hydroxyapatite and mixtures thereof are representative ceramic materials which can be used in the solid free form fabrication techniques of the invention to form dental restorations. To enhance sintering, particles can be coated with silica, for example by treating with TEOS as described below. Many possible combinations of powder and binder materials can be selected in accordance with the invention. For example, ceramic powders or ceramic fibers can be used with either inorganic or organic binder materials or with a metallic binder material; a metal powder can be used with a metallic binder or a ceramic binder; and a plastic powder can be used with a solvent binder or a plastic binder, e.g., a low viscosity epoxy plastic material. Other appropriate combinations of powder and binder materials will occur to those in the art for various applications.

The resulting color including but not limited to shade, translucency, and fluorescence, of the restoration is controlled by the pigments, opacifiers, fluorescing agents and the like, added to the powder bed components as well as components delivered through nozzles. The printed material that is used to bond successive layers can be a curable or removable organic material. When a curable material is used, the polymer-ceramic composite restoration results from the green body after curing is completed. Both natural and synthetic dispersants are available for these materials in organic vehicles. Organic dispersants have been used in the ceramics industry and are typically polymeric resins obtained form a variety of sources. They can be either water soluble, such as cellulosic binders, as used in extrusion technology, or they can be soluble in only volatile organic solvents, such as the butyral resins, as used in tape casting technology. The latter water soluble systems can be removed relatively quickly and seem particularly useful in the invention. Another example of a binder is a ceramic precursor material such as polycarbosilazane.

Inorganic binders are useful in cases where the binder is to incorporated into the final component. Such binders are generally silicate based and are typically formed from the polymerization of silicic acid or its salts in aqueous solution. An exemplary inorganic binder which can be used is tetraethylorthosilicate (TEOS). During drying, the colloidal silica aggregates at the necks of the matrix particles to form a cement-like bond. During firing, the silica flows and acts to rearrange the matrix particles through the action of surface tension forces and remains after firing.

Composite materials for use in the invention include a polymeric matrix with particulate or fiber filled components. The polymeric matrix element of the fiber-reinforced and particulate-filled composites is selected from those known in the art of dental materials, including but not being limited to polyamides, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like.

Preferred polymeric materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), polycarbonate dimethacrylate (hereinafter abbreviated "PCDMA") and ethoxylated bisphenol A dimethacrylate (hereinafter abbreviated "EBPADMA") are also commonly-used principal polymers suitable for use in the present invention.

The polymer matrix typically includes polymerization initiators, polymerization accelerators, ultraviolet light absorbers, anti-oxidants, and other additives well known in the art. The polymer matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'azobis(cyclohexanecarbo-nitrile), or other free radical initiators. The preferred fiber-reinforced polymeric matrix is a curable matrix, wherein light cure effects partial cure of the matrix, and final curing is by heat under controlled atmosphere.

The fiber-reinforced polymeric matrix may further comprise at least one filler known in the art and used in dental restorative materials, the amount of such filler being determined by the specific use of the fiber-reinforced composite. Generally, no or relatively little additional filler is present in the polymeric matrix, i.e., up to thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. Nos. 4,544,359 and No. 4,547,531 to Waknine, the pertinent portions of which are incorporated herein by reference.

The particulate-filled polymeric matrix comprises at least one filler known in the art and used in dental restorative materials, the amount of such filler being determined by the specific use of the particulate-filled composite. Generally, from about 65 to about 85% by weight of a filler is present in the particulate-filled composite and preferably, about 75 to about 83% by weight of the composite is filler in combination with about 17 to about 35% by weight and preferably about 20 to about 30% by weight and more preferably about 20 to about 26% by weight of the composite is unfilled heat curable dental resin material which makes up the polymeric matrix. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, barium sulfate, barium molybdate, barium methacrylate, barium yttrium alkoxy ($Ba_2Y(OR)_x$), strontium silicate, barium borosilicate, strontium borosilicate, borosilicate, lithium silicate, amorphous silica, ammoniated or deammoniated calcium phosphate, alumina, zirconia, tin oxide, tantalum oxide, niobium oxide, and titani. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. Nos. 4,544,359 and No. 4,547,531 to Waknine, the pertinent portions of which are incorporated herein by reference.

Preferably, the particulate-filled composite comprises an inorganic filler having an average particle size diameter of about 0.5 to about 5 microns homogeneously dispersed in an organic polymerizable monomeric matrix comprising ethoxylated dimethacrylate which is set forth in commonly owned, copending application Ser. No. 08/998,849 filed Dec. 29, 1997 which is hereby incorporated by reference. In addition, a relatively small amount of fumed silica is also predispersed within the monomeric matrix. The inorganic filler primarily comprises an X-ray opaque alkali metal or alkaline earth metal silicate such as lithium alumina silicate, barium silicate, strontium silicate, barium borosilicate, strontium silicate, barium borosilicate, strontium borosilicate, borosilicate, as well as the aforementioned materials. For purposes of illustration, and as the preferred silicate species, barium borosilicate will hereinafter be employed as being typical of the alkali metal or alkaline earth metal silicates which can be suitable employed in the present invention. The barium borosilicate exhibits an index of refraction close to that of the organic monomeric matrix in which it is dispersed. The filler can additionally contain a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap in the mismatch of refractive indices between the barium borosilicate inorganic fiber phase and the organic monomeric matrix.

Details of the preparation of the inorganic filler, which comprises a mixture of from about 5 to about 20% by weight of borosilicate glass and form about 80 to about 95% by weight barium borosilicate, and has an average particle size diameter of from about 0.5 to about 5 microns, can be found in the aforementioned U.S. Pat. Nos. 4,544,539 and 4,547,531.

The reinforcing fiber element of the fiber-reinforced composite preferably comprises ceramic, glass, carbon, graphite, polyaramid, or other fibers or whiskers known in the art, such as polyesters, polyamides, and other natural and synthetic materials compatible with the polymeric matrix. Some of the aforementioned fibrous materials are disclosed in commonly assigned copending U.S. patent application Ser. Nos. 08/907,177, 09/059,492, 60/055,590, 08/951,414 and U.S. Pat. Nos. 4,717,341 and 4,894,012 all which are incorporated herein by reference. The fibers may further be treated, for example, chemically or mechanically etched and/or silanized, to enhance the bond between the fibers and the polymeric matrix. The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension.

In some applications, it may be preferable that the binder harden relatively rapidly upon being deposited so that the next layer of particles placed on a surface of the previous layer is not subject to particle rearrangement due to capillary forces. Moreover, a hardened binder is not subject to contamination from solvents which may be used in powder deposition. In other cases, it may not be necessary that the binder be fully hardened between layers and a subsequent layer of powder particles may be deposited on a previous layer which is not yet fully hardened.

The number of restorations printed simultaneously is essentially limited by the size of the powder bed, number of nozzles and the ability to recognize and sort different restorations. To facilitate the latter operation, the robotized device can be used to pick up and sort different restorations.

It is an essential part of the present invention that components creating and/or modifying color, translucency, biocompatibility, mechanical properties (strength, fracture toughness and wear) and perceived shape are contained in the powder bed and/or delivered through nozzles. This offers a unique advantage in creating esthetics (colors, shapes) and structure (functionally gradient structures). Techniques similar to water-marks are used to create interference colors, opalescence and fluorescing effects. Other techniques are used to create perceived geometry similar to techniques used in sculpture to create impressions of the face that is perceived as a full-bodied face always looking at the observer from any angle of view.

In another embodiment of the present invention, moldable articles are fabricated in the form of feed stock (wire or filament) that is formed into the required shape of a dental restoration using a fused deposition modeling machine such as FDM2000 available from Stratasys Inc., Eden Prairie, Minn. The software used accounts for the anticipated shrinkage. The free-standing shaped article is then sintered to full density. This method can only be used for powder such as alumina or zirconia which is capable of isotropic shrinkage during sintering. U.S. Pat. No. 5,900,207 is directed to solid free form fabrication methods which is hereby incorporated by reference.

In another embodiment of the present invention, a slurry or paste of a polymer or ceramic powder is mixed with a carrier formed into a coping of a multi-layered final shape of a dental restoration using a machine similar to a fused deposition modeling machine. This machine emits or sprays beads of slurries as opposed to a fused deposition modeling machine which emits liquidfied thermoplastic materials. Examples of binder materials include curable organic materials such as mixtures of monomers or organic materials that are burned out prior to sintering. The shrinkage and setting of the materials are taken into account by oversizing the green body prior to sintering/curing.

In yet other embodiments of the present invention, other solid free-form fabrication techniques are used to make dental restorations from ceramic, glass-ceramic or composite materials.

In still another embodiment herein, SFF methods are used to provide only a skeleton of a dental restoration, e.g. a structure with interpenetrating porosity or a reticulated (cellular, honeycomb) body. This body is later infiltrated with "biological soup" containing cell cultures or peptides that can yield in-vitro grown materials similar to human tooth or bone tissues also known as biomimetic materials. For example, this infiltration media can contain biomimetically grown dental enamel crystals as described in U.S. Pat. No. 4,672,032 by Slavkin et al, which is hereby incorporated by reference. Another example of infiltration media is cultured periosteal cells as described in U.S. Pat. No. 5,700,289 to Breitbart et al.

The following examples illustrate the practice of the present invention.

EXAMPLE 1

Filament is prepared from Investment Casting Wax (ICW06, Staratasys) and thermoplastic ABS (P400, Stratasys) and equiaxed alumina powder of 5 to 10 microns particle size. The binder content is about 30 volume percent.

Using a CAD/CAM device and digitizer manufactured by CAD/CAM Ventures (Irving, Tex.), the model of a tooth preparation is digitized and the obtained CAD file is used in conjunction with an FDM2000 fused deposition modeling machine available from Stratasys Inc. (Eden Prairie, Minn.).

Using the filament containing equiaxed alumina powder in a thermoplastic matrix, single and multiunit dental restorations are formed and then subjected to binder-removal and soft-sintering cycles. The resulting porous preforms are infiltrated with glass using materials supplied by Vita Zahnfabrick (Bad Sackingen, Germany) and glass infiltration techniques used for Vita In-Ceram Alumina restorations.

EXAMPLE 2

The same CAD file as used in Example 1 is used in conjunction with a three-dimensional printing machine such as the Z402 System available from Z Corporation (MA) to print on ceramic powder and on metal powder separately. The same powder-binder mixture used above is used herein as the powder layer. A binder mixed with finely dispersed pigments is printed on the powder layer. Successive layers are deposited to form a dental restoration based on the CAD file. After the restoration is fully formed, the binder is burned out and glass is then infiltrated into the interstices. The pigment is retained in interstitial sites between the alumina particles to impart a shade to the composite.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental restoration wherein the entire restoration is formed by the method comprising:
   forming a reticulated structure of the entire restoration by a solid free form fabrication method from a composite material; and
   infiltrating the reticulated structure of the entire restoration with a biomimetic substance selected from the group consisting of cell cultures, peptides and mixtures thereof.

2. The dental restoration of claim 1 wherein the solid free form fabrication method is selected from the group consisting of three dimensional printing, ballistic particle manufacturing, fusion deposition modeling, selective laser sintering, and stereolithography.

3. The dental restoration of claim 1 wherein the composite material is selected from the group consisting of particulate filled polymeric material, fiber filled polymeric material, whisker filled polymeric material and mixtures thereof.

4. The dental restoration of claim 3 wherein the polymeric material is selected from the group consisting of polyamides, polyesters, polyolefins, polyimides, polyacrylates, polyurethanes, vinyl esters, nylon, epoxy-based materials, styrene, styrene acrylonitrile, ABS polymers, polysulfones, polyacetals, polycarbonates, polyphenylene sulfides and mixtures thereof.

5. The dental restoration of claim 3 wherein the composite material is fiber filled polymeric material comprising fibers fabricated from the group consisting of materials selected from glass, carbon, graphite, polyaramid, polyethylene and mixtures thereof.

6. The dental restoration of claim 3 wherein the composite material is particulate filled polymeric material comprising particulate material selected from the group consisting of silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide, titania poly(methacrylate) and mixtures thereof.

* * * * *

UNITED STATES PATENT AND TRADEMARK OFFICE
CERTIFICATE OF CORRECTION

| | | |
|---|---|---|
| PATENT NO. | : 6,994,549 B2 | Page 1 of 1 |
| APPLICATION NO. | : 10/035581 | |
| DATED | : January 31, 2006 | |
| INVENTOR(S) | : Guy L. Steele, Jr. | |

It is certified that error appears in the above-identified patent and that said Letters Patent is hereby corrected as shown below:

Item 54, title page, "GLOATING" should read --FLOATING--.

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

PATENT NO.       : 6,994,549 B2
APPLICATION NO.  : 09/972351
DATED            : February 7, 2006
INVENTOR(S)      : Dmitri Brodkin et al.

It is certified that error appears in the above-identified patent and that said Letters Patent is hereby corrected as shown below:

This certificate supersedes Certificate of Correction issued August 29, 2006, the number was erroneously mentioned and should be vacated since no Certificate of Correction was granted for this patent number.

Signed and Sealed this

Seventh Day of November, 2006

JON W. DUDAS
*Director of the United States Patent and Trademark Office*